US008048046B2

(12) United States Patent
Hudspeth et al.

(10) Patent No.: US 8,048,046 B2
(45) Date of Patent: Nov. 1, 2011

(54) WOUND THERAPY SYSTEM WITH HOUSING AND CANISTER SUPPORT (75) Inventors: Michael D. Hudspeth, Arnold, MO (US); Michael C. Dorsey, Edwardsville, MO (US); Kenneth M. Breitweiser, Brighton, IL (US); James M. Harr, Foristell, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 591 days.

(21) Appl. No.: 12/124,759

(22) Filed: May 21, 2008

(65) Prior Publication Data
US 2009/0292264 A1    Nov. 26, 2009

(51) Int. Cl.
*A61M 1/00*    (2006.01)
(52) U.S. Cl. ........ 604/313; 604/187; 604/192; 604/268; 604/289; 604/296; 604/300; 604/304; 604/311; 604/312; 604/315; 604/316; 604/35; 604/36; 604/119
(58) Field of Classification Search .......... 604/311, 604/312, 313, 315, 316
See application file for complete search history.

(56) References Cited

U.S. PATENT DOCUMENTS

| 730,062 | A | * | 6/1903 | Widmer .................. 248/170 |
|---|---|---|---|---|
| 3,367,332 | A | | 2/1968 | Groves |
| 3,486,504 | A | | 12/1969 | Austin, Jr. |
| 3,572,340 | A | | 3/1971 | Lloyd et al. |
| 3,712,298 | A | | 1/1973 | Snowdon et al. |
| 3,809,086 | A | | 5/1974 | Schachet et al. |
| 3,874,387 | A | | 4/1975 | Barbieri |
| 4,080,970 | A | | 3/1978 | Miller |
| 4,112,947 | A | | 9/1978 | Nehring |
| 4,112,949 | A | | 9/1978 | Rosenthal et al. |
| 4,136,696 | A | | 1/1979 | Nehring |

(Continued)

FOREIGN PATENT DOCUMENTS
DE    41 11 122 A1    4/1993
(Continued)

OTHER PUBLICATIONS

Meyer, M.D., et al., "In Surgery, Medicine and the Specialties A Manual of its Practical Application", Bier's Hyperemic Treatment, Second Revised Edition, W.B. Saunders Company, 1909.

(Continued)

*Primary Examiner* — Tatyana Zalukaeva
*Assistant Examiner* — Ilya Treyger
(74) *Attorney, Agent, or Firm* — Elias Domingo (57) ABSTRACT A system for subatmospheric pressure therapy in connection with the healing of a surgical wound is disclosed. The system may be portable or semi-portable, thereby providing the subject with the ability to be partially or completely ambulatory through the course of the treatment. The system includes a wound dressing dimensioned for positioning relative to a wound bed of a subject and a portable subatmospheric pressure mechanism dimensioned to be carried or worn by the subject. The subatmospheric pressure mechanism includes a housing, a vacuum source at least partially disposed within the housing and in fluid communication with the fluid conduit, a filter in fluid communication with the vacuum source, and a collection canister for collecting exudates from the wound bed removed under subatmospheric pressure. An elevation member is mounted with respect to the housing. The elevation member is adapted to position the housing and canister at a predetermined orientation when positioned relative to a support surface to minimize a potential of at least one of spillage of the exudates from the canister, clogging of the filter or an inappropriate canister full indication.

8 Claims, 10 Drawing Sheets

U.S. PATENT DOCUMENTS

| | | | |
|---|---|---|---|
| 4,266,545 A | 5/1981 | Moss | |
| 4,382,441 A | 5/1983 | Svedman | |
| 4,524,064 A | 6/1985 | Nambu | |
| 4,743,232 A | 5/1988 | Kruger | |
| 4,969,880 A | 11/1990 | Zamierowski | |
| 4,990,137 A | 2/1991 | Graham | |
| 4,997,438 A | 3/1991 | Nipper | |
| 5,071,104 A * | 12/1991 | Witt et al. | 251/342 |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,141,503 A | 8/1992 | Sewell, Jr. | |
| 5,149,331 A | 9/1992 | Ferdman et al. | |
| 5,152,757 A | 10/1992 | Eriksson | |
| 5,160,322 A | 11/1992 | Scheremet et al. | |
| 5,176,663 A | 1/1993 | Svedman et al. | |
| 5,178,157 A | 1/1993 | Fanlo | |
| 5,195,977 A | 3/1993 | Pollitt | |
| 5,261,893 A | 11/1993 | Zamierowski | |
| 5,263,922 A | 11/1993 | Sova et al. | |
| D364,679 S | 11/1995 | Heaton et al. | |
| 5,484,427 A | 1/1996 | Gibbons | |
| 5,527,293 A | 6/1996 | Zamierowski | |
| 5,536,233 A | 7/1996 | Khouri | |
| 5,549,584 A | 8/1996 | Gross | |
| 5,588,958 A | 12/1996 | Cunningham et al. | |
| 5,636,643 A | 6/1997 | Argenta et al. | |
| 5,645,081 A | 7/1997 | Argenta et al. | |
| 5,678,564 A | 10/1997 | Lawrence et al. | |
| 5,701,917 A | 12/1997 | Khouri | |
| 5,733,305 A | 3/1998 | Fleischmann | |
| 5,840,049 A | 11/1998 | Tumey et al. | |
| 5,911,222 A | 6/1999 | Lawrence et al. | |
| 5,944,703 A | 8/1999 | Dixon et al. | |
| 6,010,524 A | 1/2000 | Fleischmann | |
| 6,071,267 A | 6/2000 | Zamierowski | |
| 6,117,111 A | 9/2000 | Fleischmann | |
| 6,135,116 A | 10/2000 | Vogel et al. | |
| D434,150 S | 11/2000 | Tumey et al. | |
| 6,142,982 A * | 11/2000 | Hunt et al. | 604/313 |
| 6,174,306 B1 | 1/2001 | Fleischmann | |
| 6,203,563 B1 | 3/2001 | Fernandez | |
| 6,261,276 B1 | 7/2001 | Reitsma | |
| 6,325,788 B1 | 12/2001 | McKay | |
| 6,345,623 B1 | 2/2002 | Heaton et al. | |
| 6,348,423 B1 | 2/2002 | Griffiths et al. | |
| 6,352,233 B1 * | 3/2002 | Barberich | 248/676 |
| 6,398,767 B1 | 6/2002 | Fleischmann | |
| 6,406,447 B1 | 6/2002 | Thrash et al. | |
| 6,420,622 B1 | 7/2002 | Johnston et al. | |
| 6,458,109 B1 | 10/2002 | Henley et al. | |
| 6,488,643 B1 | 12/2002 | Tumey et al. | |
| 6,500,112 B1 | 12/2002 | Khouri | |
| D469,175 S | 1/2003 | Hall et al. | |
| D469,176 S | 1/2003 | Hall et al. | |
| 6,520,982 B1 | 2/2003 | Boynton et al. | |
| 6,553,998 B2 | 4/2003 | Heaton et al. | |
| D475,134 S | 5/2003 | Randolph | |
| 6,557,704 B1 | 5/2003 | Randolph | |
| D478,659 S | 8/2003 | Hall et al. | |
| 6,607,495 B1 | 8/2003 | Skalak et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| D488,558 S | 4/2004 | Hall | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,887,228 B2 | 5/2005 | McKay | |
| 6,887,263 B2 | 5/2005 | Bleam et al. | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,960,181 B2 | 11/2005 | Stevens | |
| 6,979,324 B2 | 12/2005 | Bybordi et al. | |
| 6,994,702 B1 | 2/2006 | Johnson | |
| 7,022,113 B2 | 4/2006 | Lockwood et al. | |
| 7,037,254 B2 | 5/2006 | O'Connor et al. | |
| 7,052,167 B2 | 5/2006 | Vanderschuit | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,719 B2 | 10/2006 | Rosenberg | |
| 7,128,735 B2 | 10/2006 | Weston | |
| 7,144,390 B1 | 12/2006 | Hannigan et al. | |
| 7,169,151 B1 | 1/2007 | Lytinas | |
| 7,182,758 B2 | 2/2007 | McCraw | |
| 7,195,624 B2 | 3/2007 | Lockwood et al. | |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| D544,092 S | 6/2007 | Lewis | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| D565,177 S | 3/2008 | Locke et al. | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,396,345 B2 | 7/2008 | Knighton et al. | |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,422,576 B2 | 9/2008 | Boynton et al. | |
| 2001/0031943 A1 | 10/2001 | Urie | |
| 2001/0043943 A1 | 11/2001 | Coffey | |
| 2002/0016577 A1 | 2/2002 | Ohmstede | |
| 2002/0143286 A1 | 10/2002 | Tumey | |
| 2002/0151836 A1 | 10/2002 | Burden | |
| 2003/0093041 A1 | 5/2003 | Risk, Jr. et al. | |
| 2003/0208149 A1 | 11/2003 | Coffey | |
| 2003/0212357 A1 | 11/2003 | Pace | |
| 2003/0212359 A1 | 11/2003 | Butler | |
| 2003/0219469 A1 | 11/2003 | Johnson et al. | |
| 2004/0006319 A1 | 1/2004 | Lina et al. | |
| 2004/0030304 A1 | 2/2004 | Hunt et al. | |
| 2004/0039415 A1 | 2/2004 | Zamierowski | |
| 2004/0064132 A1 | 4/2004 | Boehringer et al. | |
| 2004/0073151 A1 | 4/2004 | Weston | |
| 2004/0093026 A1 | 5/2004 | Weidenhagen et al. | |
| 2004/0122434 A1 | 6/2004 | Argenta et al. | |
| 2004/0193218 A1 | 9/2004 | Butler | |
| 2004/0233631 A1 * | 11/2004 | Lord | 361/686 |
| 2004/0241213 A1 | 12/2004 | Bray | |
| 2004/0243073 A1 | 12/2004 | Lockwood et al. | |
| 2005/0010153 A1 | 1/2005 | Lockwood et al. | |
| 2005/0020955 A1 | 1/2005 | Sanders et al. | |
| 2005/0070835 A1 | 3/2005 | Joshi | |
| 2005/0070858 A1 | 3/2005 | Lockwood et al. | |
| 2005/0085795 A1 | 4/2005 | Lockwood et al. | |
| 2005/0177190 A1 | 8/2005 | Zamierowski | |
| 2005/0182445 A1 | 8/2005 | Zamierowski | |
| 2005/0222527 A1 | 10/2005 | Miller et al. | |
| 2005/0222544 A1 | 10/2005 | Weston | |
| 2005/0261642 A1 | 11/2005 | Weston | |
| 2005/0261643 A1 | 11/2005 | Bybordi et al. | |
| 2006/0015087 A1 | 1/2006 | Risk, Jr. et al. | |
| 2006/0025727 A1 | 2/2006 | Boehringer et al. | |
| 2006/0039742 A1 | 2/2006 | Cable, Jr et al. | |
| 2006/0041247 A1 | 2/2006 | Petrosenko et al. | |
| 2006/0079852 A1 | 4/2006 | Bubb et al. | |
| 2006/0100586 A1 | 5/2006 | Karpowicz et al. | |
| 2006/0100594 A1 | 5/2006 | Adams et al. | |

| | | | |
|---|---|---|---|
| 2006/0116620 | A1 | 6/2006 | Oyaski |
| 2007/0014837 | A1 | 1/2007 | Johnson et al. |
| 2007/0021697 | A1 | 1/2007 | Ginther et al. |
| 2007/0027414 | A1 | 2/2007 | Hoffmann et al. |
| 2007/0032754 | A1 | 2/2007 | Walsh |
| 2007/0032755 | A1 | 2/2007 | Walsh |
| 2007/0032778 | A1 | 2/2007 | Heaton et al. |
| 2007/0055209 | A1 | 3/2007 | Patel et al. |
| 2007/0066946 | A1 | 3/2007 | Haggstrom et al. |
| 2007/0078366 | A1 | 4/2007 | Haggstrom et al. |

FOREIGN PATENT DOCUMENTS

| | | |
|---|---|---|
| DE | 295 04 378 U1 | 10/1995 |
| DE | 43 06 478 A1 | 12/2008 |
| EP | 0 020 662 B1 | 7/1984 |
| EP | 0 358 302 | 3/1990 |
| EP | 0 853 950 B1 | 10/2002 |
| GB | 1 549 756 | 3/1977 |
| GB | 2 195 255 A | 4/1988 |
| GB | 2 235 877 A | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1990 |
| WO | 92/19313 | 11/1992 |
| WO | 96/05873 | 2/1996 |
| WO | 9605873 | 2/1996 |
| WO | 03057307 | 7/2003 |
| WO | 03101508 | 12/2003 |
| WO | 2005009488 | 2/2005 |

OTHER PUBLICATIONS

Jeter, Katherine F., et al., "Managing Draining Wounds and Fistulae: New and Established Methods", Chronic Wound Care, 1990, pp. 240-246.

Chariker, M. E. et al. (eds), "Effective Management of Incisional and Cutaneous Fistulae with Closed Suction Wound Drainage," Contemporary Surgery, vol. 34, Jun. 1989, pp. 59-63.

B.M. Kostiuchenok, et al., "The Vacuum Effect in the Surgical Treatment of Purulent Wounds," Russian Journal: Vestnik Khirurgii, Sep. 1986, (18-21).

Y.N. Usupov, et al., "Active Wound Drainage," Russian Journal: Vestnik Khirugii, Apr. 1987, (42-45).

Yu A. Davydov, et al., "Concepts for Clinical Biological Management of the Wound Process in the Treatment of Purulent Wounds Using Vacuum Therapy," Vestnik Khirugii, Feb. 1991, 132-135).

N.A. Bagautdinov (Kazan), "Variant of External Vacuum Aspiration in the Treatment of Purulent Diseases of Soft Tissues," UDC 616-002.36 (94-96).

Chardack, et al., "Experimental studies on Synthetic Substitutes for Skin and Their Use in the Treatment of Burns," vol. 155, No. 1 (128-136).

Gorica Zivadinovic, et al., "Vacuum Therapy in the Treatment of Peripheral Blood Vessels," Conference Papers of the 5th Timok Medical Days, Majdanpek, 1986 (161-164).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

W. Fleischmann, et al., Vacuum Sealing: Indication, Technique and Results, Emr J Orthop Surg Tramatol (1995) 5:37-40.

Sherry Stoll, "Energetic Remedies—Cupping: Healing Within a Vacuum," https://www.suite101.com/article.cfm/energetic) remedies/74531, Apr. 13, 2005.

Mulder, G.D, et al., "Clinicians' Pocket Guide to Chronic Wound Repair," Wound Healing Publications Second Edition, 1991.

Yu A. Davydov, et al., "Vacuum Therapy in the Treatment of Purulent Lactation Mastitis," Russian Journal: Vesnik Khirurgii, Sep. 1986, (66-70).

Yu A. Davydov, et al., "Bacteriological and Cytological Assessment of Vacuum Therapy of Purulent Wounds", Vestnik Khirurgii, Oct. 1988, (48-52).

W. Fleischmann, "Vacuum Sealing for Treatment of Problematical Wounds", University Surgical Clinic and Polyclinic—Accident Surgery Department, WundForum Spezial—IHW 94.

Göran Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Björn, et al., "Irrigation Treatment in Split-thickness Skin Grafting of Intractable Leg Ulcers," Scand J Plast Reconstr Surg 19: 211-213, 1985.

Paul Svedman, et al., "Staphylococcal Wound Infection in the Pig: Part I. Course," Annals of Plastic Surgery, vol. 23, No. 3, Sep. 1989 (212-218).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

H. Teder, et al., "Continuous Wound Irrigation in the Pig," Journal of Investigative Surgery, vol. 3 (399-407).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Yu A. Davydov, et al., "Vacuum Therapy in treatment of Acute Purulent Diseases of Soft Tissues and Purulent Wounds," Vestnik Khirurgii, (Surgeon's Herald), MEDICINE Publishers, 1986.

US 6,216,701, 04/2001, Heaton et al. (withdrawn)

US 7,186,244, 03/2007, Hunt et al. (withdrawn)

* cited by examiner

WOUND THERAPY SYSTEM WITH HOUSING AND CANISTER SUPPORT

BACKGROUND

1. Technical Field

The present disclosure relates to treating an open wound with subatmospheric pressure, and, more specifically, relates to a semi-portable or portable therapy system including a support mechanism for maintaining the subatmospheric mechanism at a predetermined orientation to minimize a potential of either spillage of the exudates from the exudates canister, clogging of the filter or an inappropriate canister full indication.

2. Description of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy also known as suction or vacuum therapy has been used in treating and healing wounds. Application of negative pressure, e.g. reduced or subatmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound to be covered to facilitate suction at the wound area. A fluid conduit provides fluid communication between the interior of a wound covering and an external vacuum source. Atmospheric gas, wound exudates, or other fluids may be drawn from the reservoir through the fluid conduit to stimulate healing of the wound. Exudates drawn from the reservoir may be deposited in a collection canister.

SUMMARY

Accordingly, the present disclosure is directed to a system for subatmospheric pressure therapy in connection with the healing of a surgical wound. The system may be portable or semi-portable, thereby providing the subject with the ability to be partially or completely ambulatory through the course of the treatment. Generally stated, the system includes a wound dressing dimensioned for positioning relative to a wound bed of a subject and a portable subatmospheric pressure mechanism dimensioned to be carried or worn by the subject. The subatmospheric pressure mechanism includes a housing, a vacuum source at least partially disposed within the housing and in fluid communication with the fluid conduit, a filter in fluid communication with the vacuum source, and a collection canister for collecting exudates from the wound bed removed under subatmospheric pressure. An elevation member is mounted with respect to the housing. The elevation member is adapted to position the housing and canister at a predetermined orientation when positioned relative to a support surface to minimize a potential of at least one of spillage of the exudates from the canister, clogging of the filter or an inappropriate canister full indication. The elevation member may be a stand member which is positionable on the support surface. The stand member may be dimensioned to define a cradle for at least partial reception of the housing or the canister.

In the alternative, the stand member includes at least two support members. The support members may be adapted for relative movement, e.g., pivotal movement, to vary a dimensioning of the stand member.

In another embodiment, the elevation member includes a leg member mounted to one of the housing or the collection canister. The leg member is movable between a closed position where the leg member is proximate the housing and an open position where the leg member depends from the housing at a predefined angular orientation to support the housing on the support surface. Means for releasably securing the leg member in the open position and the closed position may be provided.

The elevation member may include a hinge member mounted to one of the collection canister and the housing. The hinge member defines first and second hinge segments connected to each other through hinge means. The first and second hinge segments are adapted to pivot relative to each other about the hinge means from an initial ambulatory position to a deployed position to support the subatmospheric pressure mechanism on the support surface. The collection canister may include at least one step depending therefrom and engageable with an edge of the first hinge segment to secure the hinge segment in the deployed position. The collection canister may include a plurality of spaced steps to vary an orientation of the subatmospheric pressure mechanism.

BRIEF DESCRIPTION OF THE DRAWINGS

Various embodiments of the wound dressing system of the present disclosure are described herein with reference to the drawings wherein.

DESCRIPTION OF THE PREFERRED EMBODIMENT(S)

The wound therapy system of the present disclosure promotes healing of a wound via the use of a wound dressing and a portable subatmospheric pressure mechanism. Generally, the portable subatmospheric pressure mechanism applies subatmospheric pressure to the wound to effectively remove wound fluids or exudates captured by the composite wound dressing, and to increase blood flow to the wound bed and enhance cellular stimulation of epithelial and subcutaneous tissue. The wound therapy system may be entirely portable, i.e., it may be worn or carried by the subject such that the subject may be completely ambulatory during the therapy period. The wound therapy system including the subatmospheric pressure mechanism and components thereof may be entirely disposable after a predetermined period of use or may be individually disposable whereby some of the components are reused for a subsequent therapy application.

The wound therapy system of the present disclosure promotes healing of a wound in conjunction with subatmospheric negative pressure therapy. The system may incorporate a variety of wound dressings, subatmospheric mechanisms including pressure sources and pumps, and collection canisters. An elevation or support mechanism associated with the subatmospheric support mechanism maintains the housing and exudates collection canister at a predetermined, e.g., generally upright orientation to minimize spillage of the exudates from the exudates collection canister, clogging of the filter or an improper full indication.

The attached figures illustrate an exemplary embodiment(s) of the present disclosure and are referenced to describe the embodiments depicted therein. Hereinafter, the disclosure will be described by explaining the figures wherein like reference numerals represent like parts throughout the several views.

Figure 1:
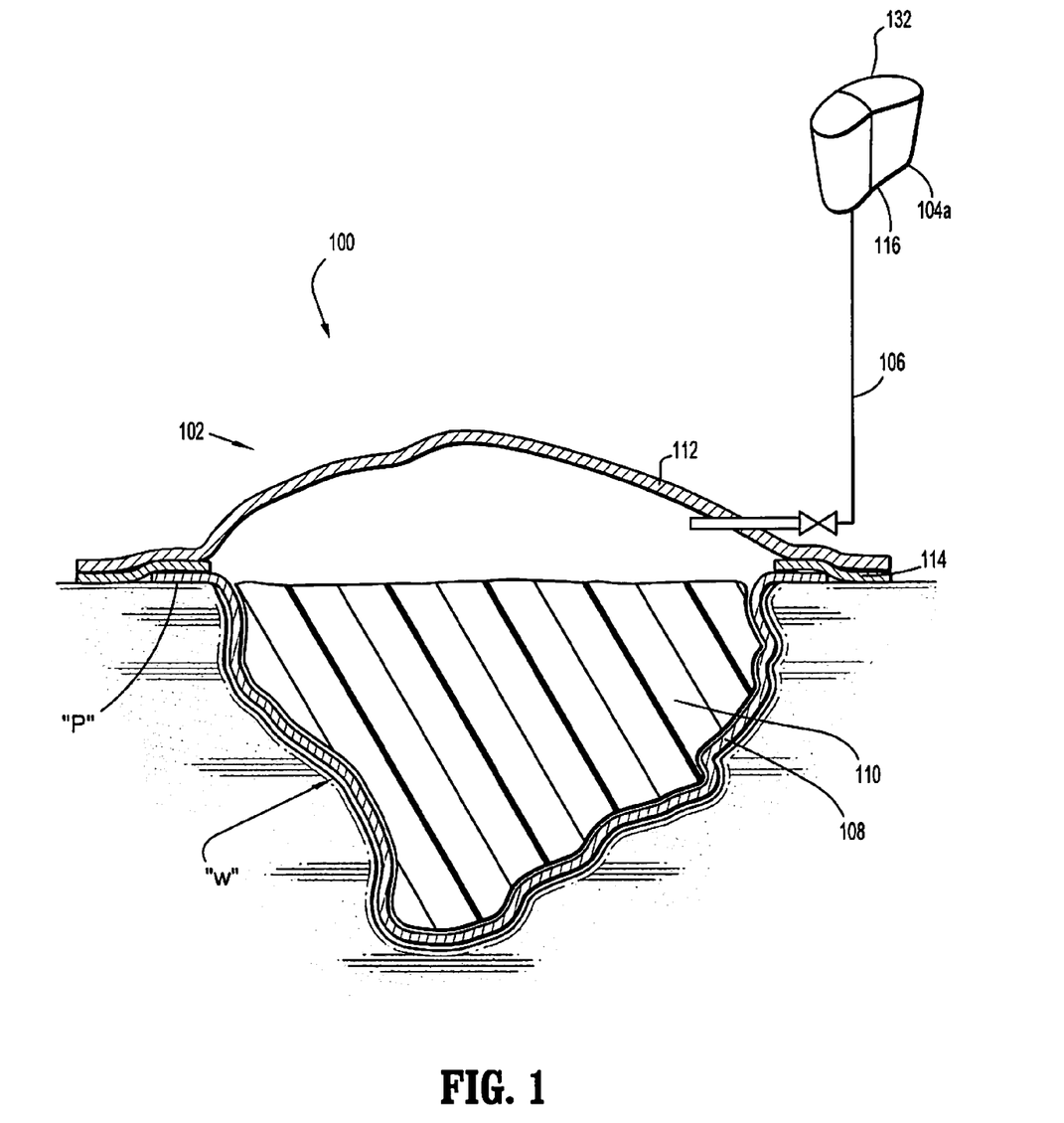
FIG. 1 is a perspective view of the portable wound therapy system of the present disclosure illustrating the wound dressing and the subatmospheric pressure mechanism.

Referring now to FIG. 1, the wound therapy system 100 of the present disclosure is illustrated. Wound therapy system 100 includes composite wound dressing 102 and subatmospheric pressure mechanism 104 which is in fluid communication with the wound dressing 102 through conduit, identified schematically as reference numeral 106.

Wound dressing 102 may include several components, namely, wound contact layer or member 108, a wound packing member or filler 110 supported by the contact member 108 and outer layer or cover member 112. Wound contact member 108 is adapted to substantially conform to the topography of a wound bed "w". Wound contact member 108 is substantially porous to permit exudates to pass from the wound bed "w" through the wound contact member 108. The porosity of contact member 108 may be adjusted by varying the size of the apertures or perforations both in diameter or size and in distribution about the contact member 108. Thus, fluid flow from the wound may be optimized and adherence of the contact member 108 to the wound bed may be minimized. Wound contact member 108 may also be non-adherent. This configuration allows fluid and exudates to flow uninhibited through wound contact member 108 with minimal "sticking" of wound contact member 108 to the wound bed "w" while maintaining proper wound moisture balance. FIG. 1 illustrates contact member 108 with pores 108a. The pore 108a may be equal in size or diameter or have varying or random sizes and dimensions.

The passage of wound exudates through the wound contact member 108 is preferably unidirectional such that wound exudates do not flow back to the wound bed "w". This unidirectional flow feature could be in the form of directional apertures imparted into the material layer, a lamination of materials of different fluid transfer or wicking capability or a specific material selection that encourages directional exudates flow. However, a bidirectional layer for the purposes of supplying medicine or anti-infectives to the wound bed "w" is also envisioned and will be described hereinafter.

In addition, agents such as hydrogels and medicaments could be bonded or coated to the contact member 108 to reduce bioburden in the wound, promote healing, increase blood flow to the wound bed and reduce pain associated with dressing changes or removal. Medicaments include, for example, antimicrobial agents, growth factors, antibiotics, analgesics, nitric oxide debridement agents, oxygen enrichment and the like. Furthermore, when an analgesic is used, the analgesic could include a mechanism that would allow the release of that agent prior to dressing removal or change.

Contact member 108 may be constructed from a variety of different materials. These may include but are not limited to synthetic non absorbable polymer fibers such as carbonized polymers, polyethylene (PE), polypropylene (PP), polytetrafluoroethylene (PTFE), Nylon, aramids, Kevlar, polyethylene terephthalate (PET) or natural fibers such as cellulose. It is envisioned that contact member 108 may be transparent to allow improved visual capacity and a better view of wound bed "w". Moreover, contact member 108 may be constructed of a fabric which could be woven, nonwoven (including melt blown), knitted or composite structures such as spun bonded fabrics. Exemplary materials used as contact member 108 are sold under the trademark EXCILON™ or XEROFLOW™ both by Tyco Healthcare Group LP (d/b/a Covidien).

Wound packing member 110 of wound dressing 102 is intended to absorb and transfer wound fluid and exudates. Exemplary absorbent materials include foams, nonwoven composite fabrics, hydrogels, cellulosic fabrics, super absorbent polymers, and combinations thereof. Typically, wound packing member 110 can contain or absorb up to about 100 cubic centimeters (cc) or more of wound fluid. Preferably, the absorbent material includes the antimicrobial dressing sold under the trademark KERLIX® AMD by Tyco Healthcare Group LP (d/b/a Covidien). In one preferred embodiment, packing member 110 could be preformed or shaped to conform to varying shapes of the wound bed. Those skilled in the art will recognize that packing member 110 can be formed in any suitable shape. Packing member 110 may include multiple layers. In another performed embodiment, the packing member 110 may be constructed in layers of varying absorbent materials to assist in directional flow or exudates away from the wound.

Additionally, with reference to FIG. 1, the packing member 110 may include hydrophobic materials such as continuous synthetic fibers intended to transfer wound fluids under negative pressure. The synthetic fibers may be constructed from polymeric materials such as polypropylene, polyethylene, polyester and other like polymers. The continuous fibers may be arranged in bundles or multiple fibers to help facilitate loft or form to the wound packing member 110, e.g., in a tow arrangement depicted in FIG. 1B. Further, the fiber bundles may be bonded at given lengths using straps or some form of adhesive, into a fused zone 110b. The fused zone 110b may be an area to cut the fiber bundle to a selected length to adapt the wound packing member 110 optimally to various wound sizes.

Alternatively, wound packing member 110 could be hydrophobic/non-absorbent materials to minimize wound fluids near the wound. Examples of such materials may be fibers in a tow arrangement, felts or foam composed of PTFE, PE, PET or hydrophilic materials treated with silicon or PTFE solution.

Additionally, absorbent or non-absorbent packing member 110 could be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, healing factors such as vitamins, growth factors, nutrients and the like, as well as a flushing agent such as isotonic saline solution.

In the alternative, absorbent or non-absorbent packing member 110 may include a bead arrangement as disclosed in commonly assigned U.S. Patent Publication No. 2007/0185463, the entire contents of which is incorporated herein by reference. The beads disclosed in the '463 publication are preferably substantially rigid so as to maintain their shapes for at least a predetermined period of time during healing. The beads when arranged within the wound bed "w" define spaces or passages therebetween to permit wound exudates to pass through the passages. The sizes of the beads may vary, but they should be sized to achieve the proper pore size through the bead arrangement to facilitate cell proliferation and allow fluid and air to be evacuated from the wound. A porosity in the range of 10-1000 μm has been found beneficial in stimulating cell proliferation and in allowing fluid and air to be evacuated from the wound. The beads may work in conjunction with contact member 108 to conform to the wound bed "w" while allowing drainage of wound exudates and release of air from the wound bed "w" without clogging. As the negative pressure is applied, the beads will move and readjust their respective positions to prevent painful ingrowth that can occur with current foam dressing designs.

Referring again to FIG. 1, outer member or wound covering 112 encompasses the perimeter of the wound dressing 100 to surround wound bed "w" and to provide a liquid-tight seal around the perimeter "p" of the wound bed "w". For instance, the sealing mechanism may be any adhesive bonded to a layer that surrounds the wound bed "w". The adhesive must provide acceptable adhesion to the tissue surrounding the wound bed "w", e.g., the periwound area, and be acceptable for use on the skin without contact deteriorization (e.g., the adhesive should preferably be non-irritating and non-sensitizing). The adhesive may be permeable or semi permeable to permit the contacted skin to breathe and transmit moisture. Additionally, the adhesive could be activated or de-activated by an external stimulus such as heat or a given fluid solution or chemical reaction. Adhesives include, for example, medical grade acrylics like the adhesive used with CURAFOAM ISLAND™ dressing of Tyco Healthcare Group LP (d/b/a Covidien) or any silicone or rubber based medical adhesives that are skin friendly and non irritating. Wound covering member 112 may be provided with an adhesive backing and/or alternatively, an adhesive may be applied to the wound covering 112 and/or skin during the procedure. As a further alternative, an annular shape adhesive member 114 may be interposed between the periphery of wound covering 112 and overlapping the periphery of contact member 108 to secure the wound covering 112 about the wound "w".

Wound covering 112 is typically a flexible material, e.g., resilient or elastomeric, that seals the top of wound dressing 102 to prevent passage of liquids or contamination to and from the wound dressing 102. Exemplary flexible materials include the semipermeable transparent dressing manufactured under the trademark Polyskin II® by Tyco Healthcare Group LP (d/b/a Covidien). Polyskin II® is a transparent semi permeable material which permits passage of moisture or water vapors from the wound site through the dressing 102, while providing a barrier to microbes and fluid containment. Alternative films could be manufactured from polyurethanes, breathable polyolefins, copolyesters, or laminates of these materials. The transparency of wound covering 112 permits a visual review of the status of the wound dressing 102 and the saturation level of the packing member 110. As an alternative, outer covering member 112 may be impermeable to moisture vapors.

Outer suitable wound dressing are disclosed in commonly assigned U.S. Patent Publication Nos. 2007/0078366, 2007/0066946 and 2007/0055209, the entire contents of each disclosure being incorporated herein by reference.

Referring now to the schematic diagram of FIG. 2, in conjunction with FIG. 1, subatmospheric pressure mechanism 104 will be discussed. Subatmospheric pressure mechanism 104 includes housing 116, vacuum source or pump 118 disposed within the housing 116, actuator or motor 120 disposed with the housing 116 for activating the vacuum source 118 and power source 122 mounted relative to the housing 116. Vacuum source or pump 118 may be any miniature pump or micropump that is biocompatible and adapted to maintain or draw adequate and therapeutic vacuum levels. Preferably, the vacuum level to be achieved is in a range between about 75 mmHg and about 125 mmHg. Vacuum source or pump 118 may be a pump of the diaphragmatic, peristaltic or bellows type or the like, in which the moving part(s) draw exudates out of the wound bed "w" into the wound dressing 102 by creating areas or zones of decreased pressure e.g., vacuum zones with the wound dressing 102. This area of decreased pressure preferably communicates with the wound bed "w" to facilitate removal of the fluids therefrom and into the absorbent or non-absorbent packing member 110. Vacuum source or pump 118 is actuated by actuator 120 which may be any means known by those skilled in the art, including, for example, AC motors, DC motors, voice coil actuators, solenoids, etc. Actuator 120 may be incorporated within pump 118.

Power source 122 may be disposed within housing 116 or separately mountable to the housing 116. A suitable power source 122 includes alkaline batteries, wet cell batteries, dry cell batteries, nickel cadmium batteries, solar generated means, lithium batteries, NiMH batteries (nickel metal hydride) each of which may be of the disposable or rechargeable variety.

Additional components of subatmospheric pressure mechanism may include pressure sensor 124 to monitor pressure adjacent the vacuum source or pump 118 or selected locations displaced from the pump 118, and regulation or control means 126. The control means 126 may incorporate a motor controller/driver 128 including processing and drive circuitry to control or vary the drive voltage to the motor of the vacuum source or pump 118 responsive to the pressure sensed by the pressure sensor 124. The output of the motor of the vacuum source 118 may be increased or decreased, or initiated or discontinued, as controlled by control means 126. Pressure sensor 124 would also provide information to assist in detecting a leak in the wound therapy system 100 if the optimal subatmospheric pressure is not achieved. Regulation or control means 126 may also have an alarm such as a visual, audio or tactile sensory alarm (e.g., vibratory etc.) to indicate to the user when specific conditions have been met (e.g., the desired vacuum level or loss of vacuum) as may be associated with a full exudates container. Pressure sensor 124 may be replaced or supplemented with any other type of sensor or detector for measuring or detecting a characteristic or condition of the wound bed "w". Additional sensors contemplated include thermal sensors, bacterial sensors, oxygen sensors, moisture sensors, etc. which will provide the clinician with additional diagnostic information.

Referring again to FIG. 1, wound therapy system 100 further includes collection canister 132 which collects the exudates removed from the wound "w" during therapy through tubing 106. Collection canister 132 is preferably associated with housing 116 and may be incorporated within the housing 116 or releasably connected to the housing 116 by conventional means. Collection canister 132 is substantially rigid and defines an internal chamber in fluid communication with tubing 106. As an alternative, the collection canister 132 may include a flexible unit contained within housing 116 and removable to facilitate disposal of would fluids. In embodiments, at least a portion of collection canister 132 may be transparent to assist in evaluating the color, quality, or quantity of wound exudates. A transparent canister thus may assist in determining the remaining capacity of the canister or when the canister should be replaced. In the alternative, collection canister 132 may be relatively opaque. A filter may be incorporated within collection canister 132. The filter is preferably a hydrophobic filter in communication with vacuum pump 118 and being adapted to permit air to pass while preventing passage of liquid. Thus, the wound exudates may be drawn into collection canister 132 via vacuum pump 118 and is prevented from communicating to the vacuum pump 118 by the filter. When the exudate contacts and/or covers the filter in the event collection canister 132 is full, the vacuum supply to collection canister 132 may be halted. Circuitry or logic associated with control means 126 may sound an audible alarm and discontinue operation of vacuum pump 118.

Figure 2:
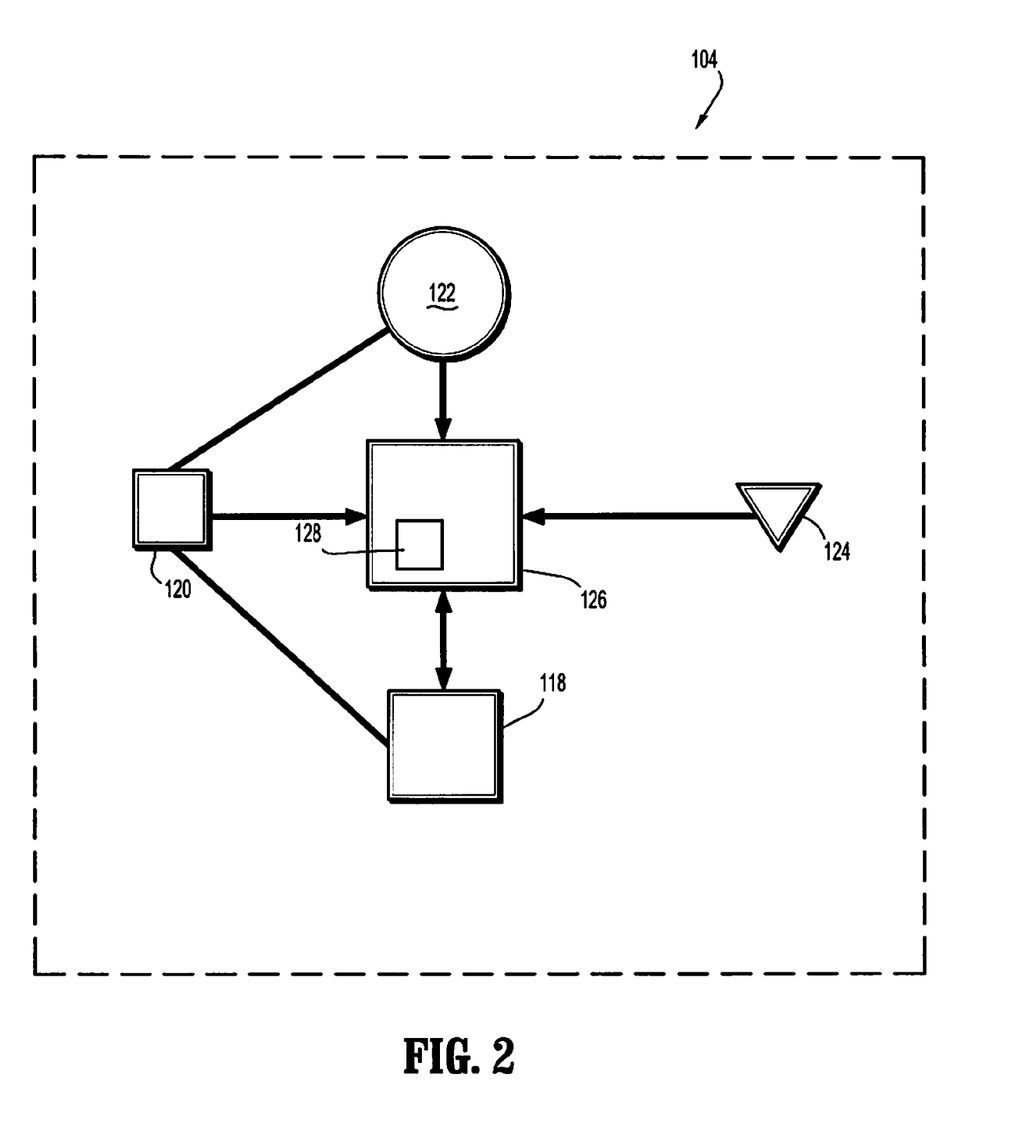
FIG. 2 is a schematic diagram of various components of the subatmospheric pressure mechanism.

In the subatmospheric pressure mechanism 104 of FIGS. 1 and 2, vacuum source or pump 118, motor 120, pressure sensor 124 and control means 126 are incorporated into housing 116. Pressure sensor 124 may also be displaced from the housing of the micropump 118, e.g., adjacent packing member 110 at a location displaced from housing 120, and connected to the control means 126 through an electrical connection. Power source 122 may be incorporated within housing 116 or may be releasably connected to the housing 116 through conventional means.

Figure 3:
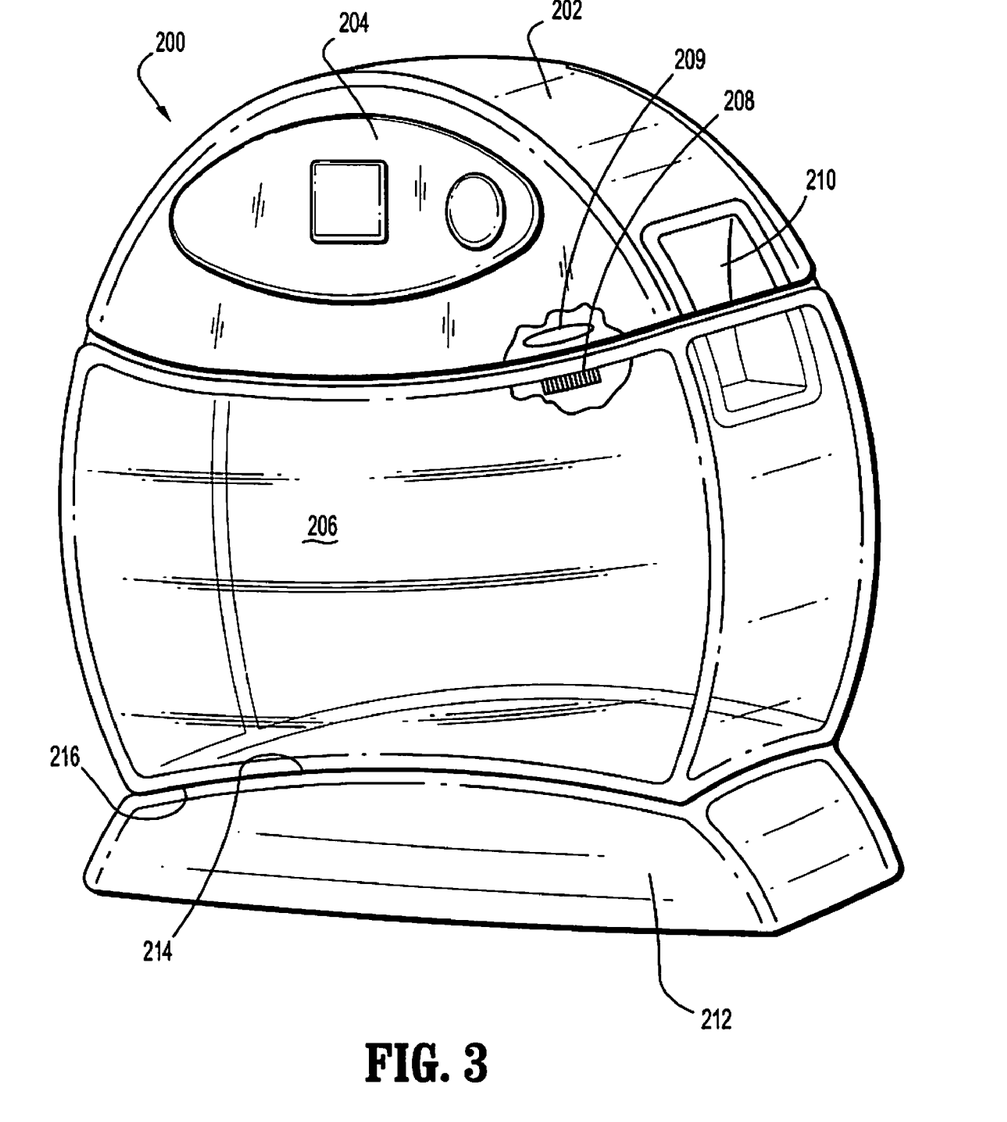
FIG. 3 is a perspective view illustrating one embodiment of an elevation member for supporting the subatmospheric pressure mechanism.

Referring now to FIG. 3, another embodiment of the subatmospheric pressure mechanism 104 is illustrated. Subatmospheric pressure mechanism 200 is dimensioned to be carried or worn by the subject. Subatmospheric pressure mechanism 200 includes housing 202 which incorporates a vacuum source and additional circuitry, software or logic as discussed hereinabove. Housing 202 may further include control panel 204 for controlling operation of subatmospheric pressure mechanism 200. Subatmospheric pressure mechanism 200 further includes collection canister 206 for collecting the wound exudates. Collection canister 206 may incorporate filter 208 (shown in cut-away) adjacent the port 209 which establishes fluid communication between the vacuum source and the interior of collection canister 206. Housing 202 and collection canister 206 may incorporate means for releasably connecting the collection canister 206 and the housing 202. Such means may be in the form of a release latch mechanism 210 generally depicted in FIG. 3.

The system further includes elevation member 212 which, in this embodiment is in the form of a stand. Elevation member 212 is adapted to position housing 202 and canister 206 in a predetermined orientation when positioned relative to a support surface such as a table, desk or the like. In one embodiment, elevation member 212 supports housing 202 and canister 206 in a general upright or vertical condition. Elevation member 212 may define an arcuate or sloped upper surface 214 corresponding to an arcuate or sloped lower surface 216 of collection canister 206 to facilitate positioning and retention of the collection canister 206 on the elevation member 212. It is further contemplated that the respective upper and lower surfaces 214, 216 of elevation member 212 and collection canister 206 may incorporate cooperating protrusions, recesses or undulations to further enhance retention capabilities and characteristics of the system.

Figure 4A:
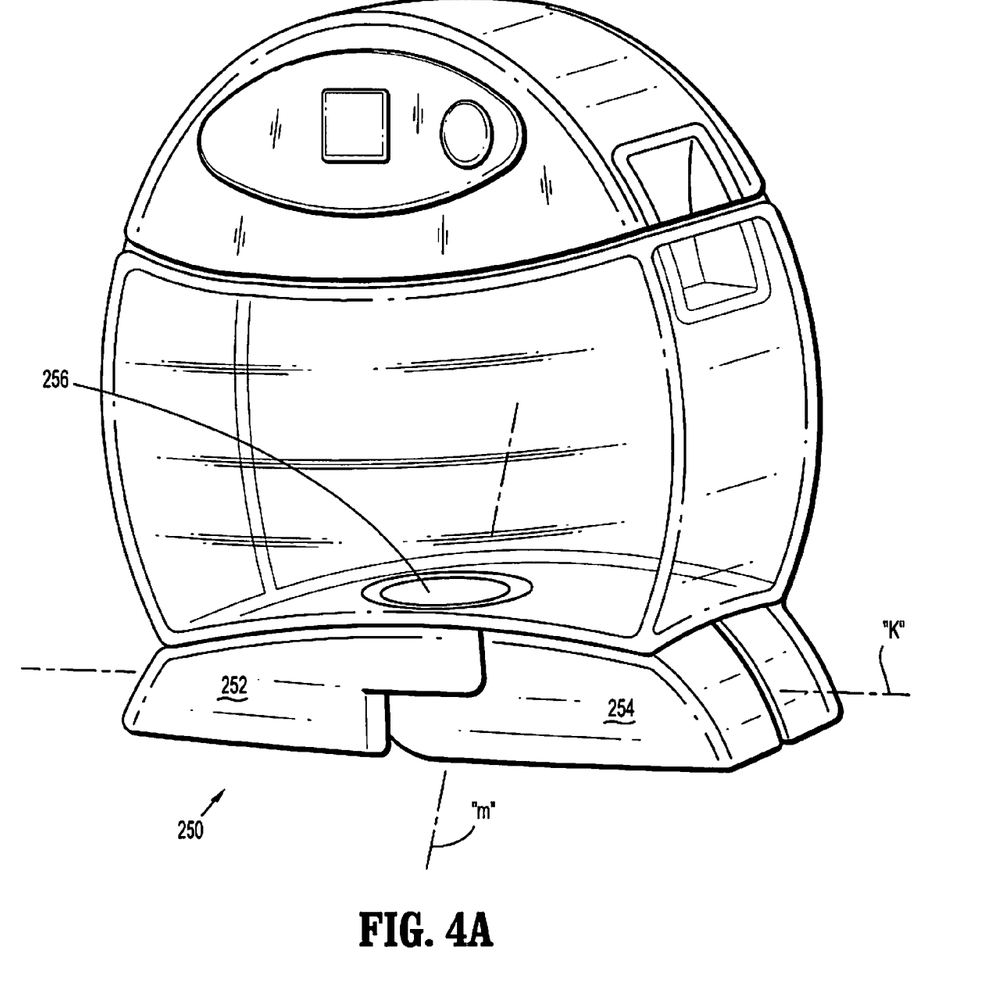
FIG. 4A is a perspective view of another embodiment of the elevation member for supporting the subatmospheric pressure mechanism incorporating a pair of pivoting foot supports depicted in a first initial position.
Figure 4B:
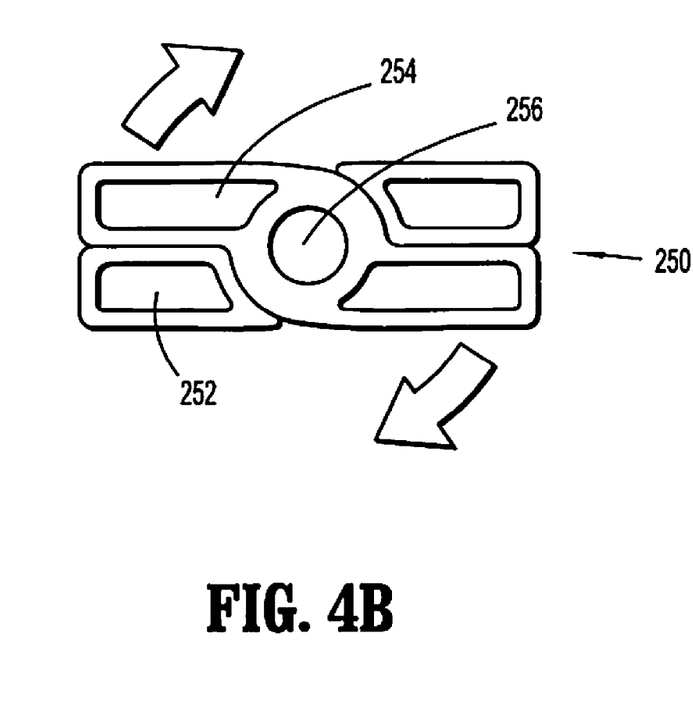
FIG. 4B is a bottom plan view of the stand of FIG. 4A illustrating the pivoting foot supports.
Figure 4C:
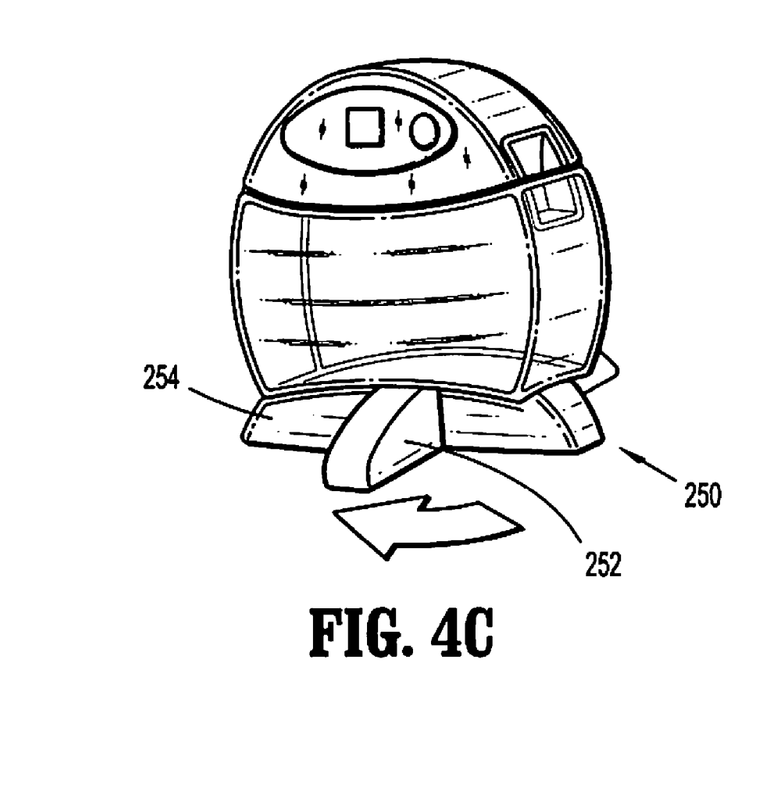
FIG. 4C is a perspective view similar to the view of FIG. 4A illustrating the foot supports in a second pivoted position.

FIGS. 4A-4C illustrate an alternate embodiment of elevation member 250. In accordance with this embodiment, elevation member 250 includes first and second foot support members 252, 254. First and second support members 252, 254 are adapted for relative pivotal movement about, e.g., pivot element 256, which extends at least partially through the first and second support members 252, 254. First and second support members 252, 254 may move from the first or initial position of FIGS. 4A and 4B and the second or pivoted position of FIG. 4C to increase the effective longitudinal and traverse dimensions of elevation member 250, i.e., relative to longitudinal and transverse axes "K" and "M" respectively, to thereby provide enhanced supporting characteristics to the elevation member 250. First and second support members 252, 254 may be releasably secured at either or both the first and second positions, by, e.g., locking detent means, pawl and ratchet means, snap-lock means or the like. In addition, first and second support members 252, 254 may be positioned and possibly secured at any positions intermediate the first and second positions as well.

Figures 5A, 7:
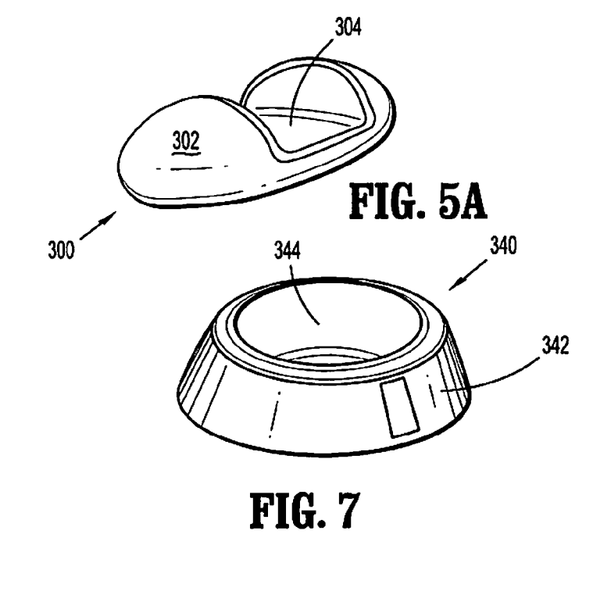
FIGS. 5A-5C are perspective, top plan and side plan views of another embodiment of an elevation member incorporating a base with a cradle.
FIGS. 7-9 are perspective views of additional embodiments of the elevation member.
Figure 5B:
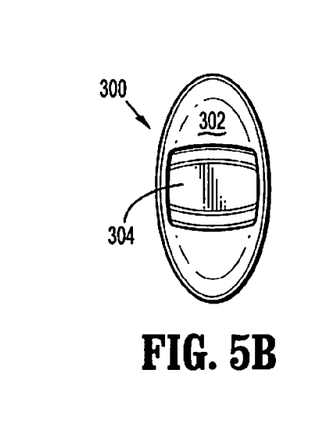
Figure 5C:
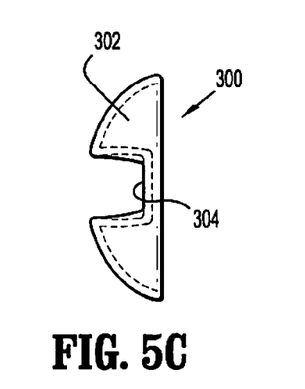

FIGS. 5A-5C illustrate another embodiment of an elevation member for accommodating the subatmospheric pressure mechanism. Elevation member 300 has base 302 defining cradle or recess 304 for at least partially receiving collection canister 206. Cradle 304 enhances releasable securement of subatmospheric pressure mechanism within elevation member by at least partially surrounding the lower portion of the collection canister 206.

Figure 6A:
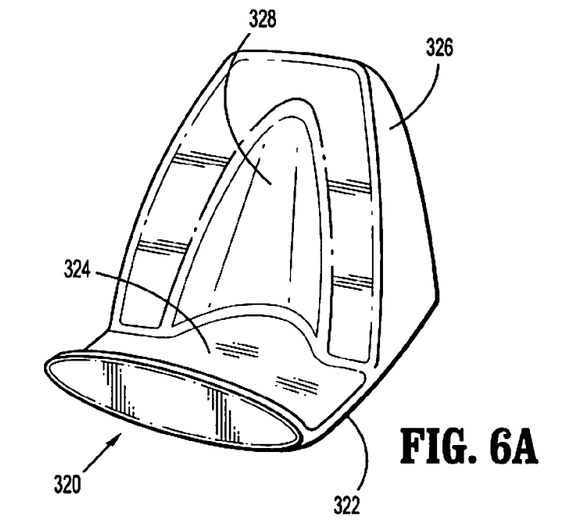
FIGS. 6A-6B are perspective and side plan views of another embodiment of the elevation member of FIGS. 5A-5C.
Figure 6B:
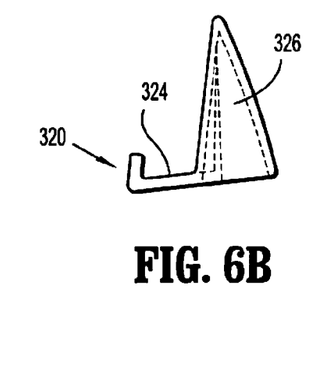

FIGS. 6A-6B illustrate another alternate embodiment of an elevation member 320. Elevation member 320 defines base 322 having cradle 324, and has upstanding wall member 326 depending in a general vertical direction from the base 322. Wall member 326 may extend in a general oblique relation from base 322 to slightly angulate the collection canister and the housing when mounted within cradle 324. This minimizes the potential of the collection canister and the housing from inadvertent tilting or falling. Wall member 326 may incorporate recess 328 to capture collection canister 206.

FIG. 7 illustrates another embodiment of elevation member 340 including circular base 342 (in cross-section) having a circular recess or cradle 344. In one embodiment, collection canister 206 may have a circular lower portion to correspond with circular cradle 344 of base 342 for reception therein.

Figure 8:
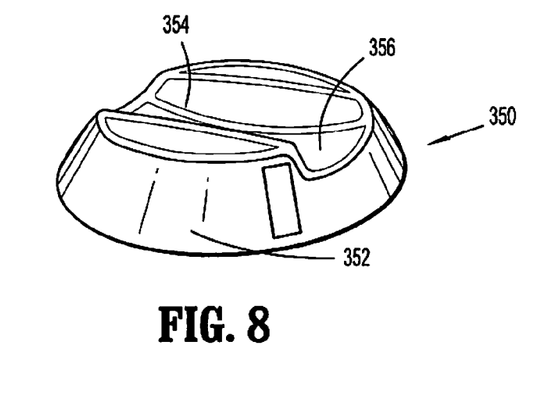

FIG. 8 illustrates another embodiment of elevation member 350 including circular base 352 (in cross-section) having an elongated or rectangular-shaped recess or cradle 354. Collection canister 206 may have a correspondingly rectangular-shaped cross-section for at least partial reception within cradle 354. Circular base 352 may have an arcuate lower surface adjacent cradle 354 to also correspond to a similar configuration of the lower surface of collection canister 206 to further assist in retention of the collection canister 206 within base 352.

Figure 9:
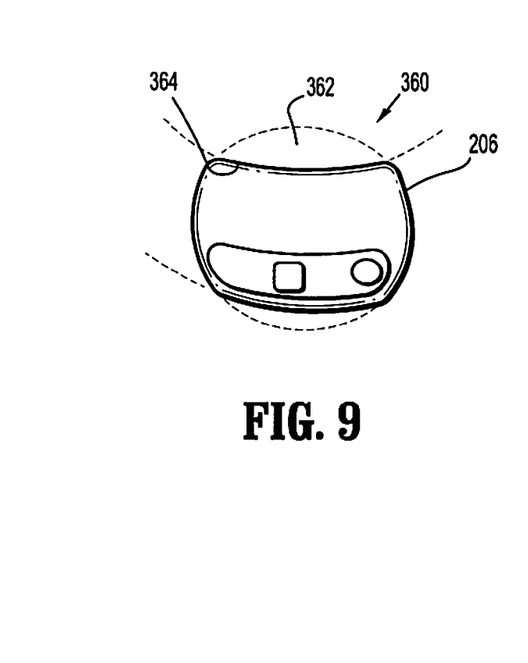

FIG. 9 is a top view illustrating an elevation member 360 including base 362 and elongated cradle 364 which is generally arcuate or curved as shown. In one embodiment, collection canister 206 incorporates an arcuate profile corresponding to the arcuate arrangement of elongated cradle 364 whereby the collection canister 206 is at least partially received within the cradle 364. This arrangement ensures that collection canister 206 is positioned at a defined orientation relation to base 362. Collection canister 206 may be slid within cradle 364 during insertion and mounting thereof.

Figure 10A:
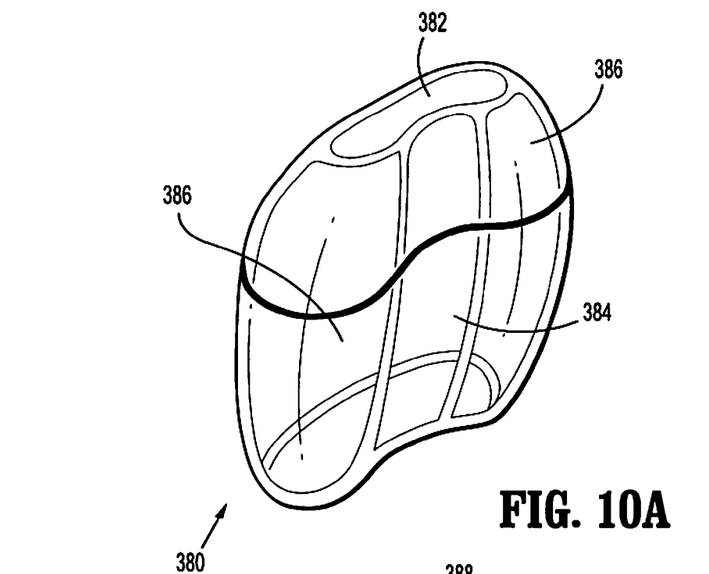
FIGS. 10A-10B are perspective and side plan views of an additional embodiment illustrating a self supporting subatmospheric pressure mechanism.
Figure 10B:
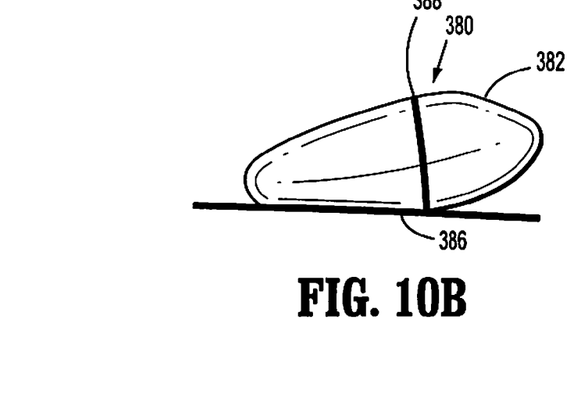

FIGS. 10A-10B illustrate another embodiment of subatmospheric pressure mechanism 380. Subatmospheric pressure mechanism 380 is self-supporting, i.e., it is devoid of a separate elevation member. In accordance with this embodiment, housing 382 and collection canister 384 collectively define a pair of elongated, bulbous sections 386 extending for at least part of the length of subatmospheric pressure mechanism 380. Elongated sections 386 are sufficiently wide to support the subatmospheric pressure mechanism 380 at a predetermined orientation when positioned on a table or the like. It is appreciated that the components of the subatmospheric pressure mechanism 380 of this embodiment are arranged within housing 382 and canister 384 to ensure proper operation of the subatmospheric pressure mechanism when in the position of FIG. 10B. For example, the hydrophobic filter and vacuum port may be positioned adjacent the upper portion of the subatmospheric pressure mechanism, e.g., at the location identified by reference numeral 388 to ensure that the filter and port are not covered or clogged when positioned properly on the support surface during operation.

FIGS. 11A-11D illustrate an alternate embodiment of subatmospheric pressure mechanism 400. In accordance with this embodiment, elevation member 402 is an articulating leg member 402 connected to collection canister 404. In particular, leg member 402 is adapted for pivotal movement relative to collection canister 404 between a first ambulatory condition (depicted in phantom in FIG. 11A) and a second supporting position. In the first ambulatory condition, leg member 402 is in juxtaposed relation with collection canister 404 and may be at least partially received within corresponding recess 406 of collection canister 404. Leg member 402 may be pivotally connected to collection canister 404 by any means including a pivot pin or about a living hinge. Leg member 402 is adapted to position subatmospheric pressure mechanism 400 in an oblique condition relative to a support surface.

Figure 11A:
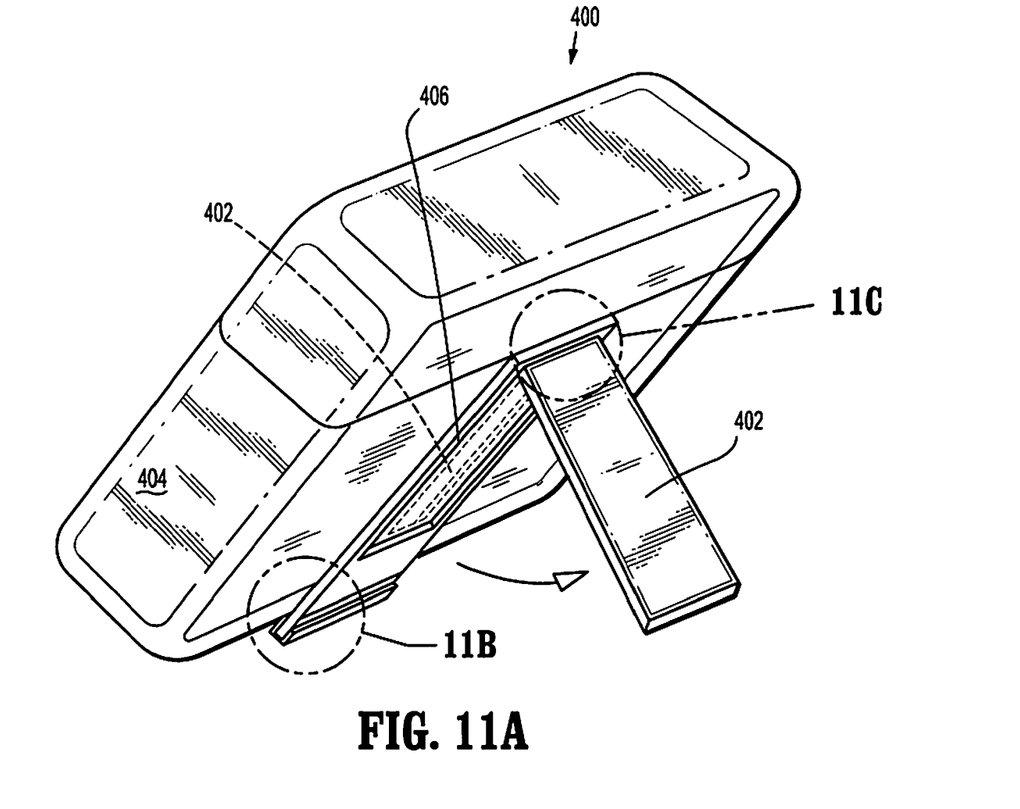
FIG. 11A is a perspective view of another alternate embodiment of the subatmospheric pressure mechanism incorporating an articulating leg member.
Figure 11B:
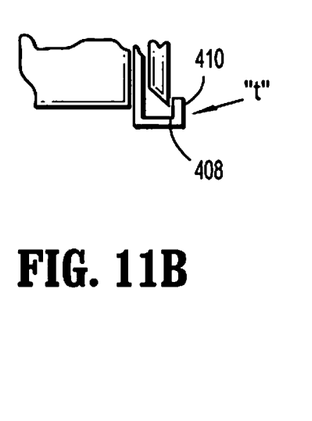
FIG. 11B is an isolated view illustrating an actuation button for deploying the leg member of the embodiment of FIG. 11B.

As best depicted in FIGS. 11A-11B, an actuation or release button 408 may be associated with leg member 402 to selectively release and/or deploy leg member 402 to assume the second supporting position. In one embodiment, actuation button 408 is disposed adjacent the lower surface of collection canister 404. Actuation button 408 incorporates a lip or detent 410 which receives the lower edge of the leg member 402 to secure the leg member 402 in the first ambulatory position. When subatmospheric pressure mechanism, i.e., collection canister 404 and the housing 410, is placed on a support surface, actuation button 408 engages the support surface and is displaced in the direction of directional arrow "t" to release the lower surface of leg member 402. Actuation button 408 may be mounted to collection canister 404 via a living hinge or the like which permits displacing movement relative to collection canister 404. Once released, leg member 402 may be moved manually to the second supporting position.

Figure 11C:
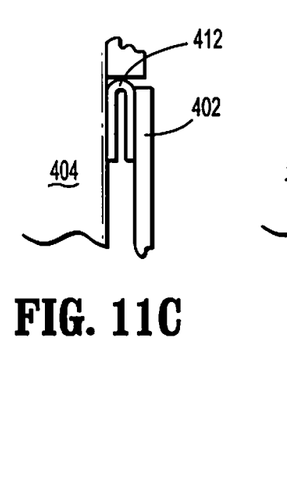
FIG. 11C is an isolated view illustrating a deployment spring for automatically deploying the leg member of the subatmospheric pressure mechanism.
Figure 11D:
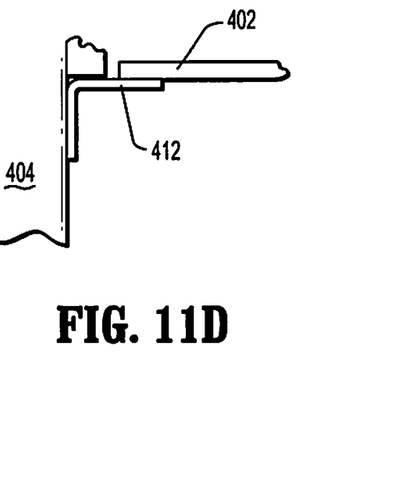
FIG. 11D illustrates the deployment spring in a deployed position.

As a further alternative, leg member 402 may be normally biased toward the second supporting position by a spring or bias means. Such bias means may include a coil spring mounted about a pivoting pin operatively connecting the collection canister 404 and leg member 402. In the alternative, the spring means may incorporate a general "L"-shaped spring or tab 412 mounted between collection canister 404 and leg member 402 as shown in FIGS. 11C-11D. Tab 412 may be a resilient polymeric or metal material adapted to flex when leg member 402 is moved toward the first ambulatory condition as depicted in FIG. 11C, and return toward its normal L-shaped condition biasing the leg member 402 outwardly relative to collection canister 404 as depicted in FIG. 11D upon actuation or release of actuation button 410.

Figures 12A, 12B:
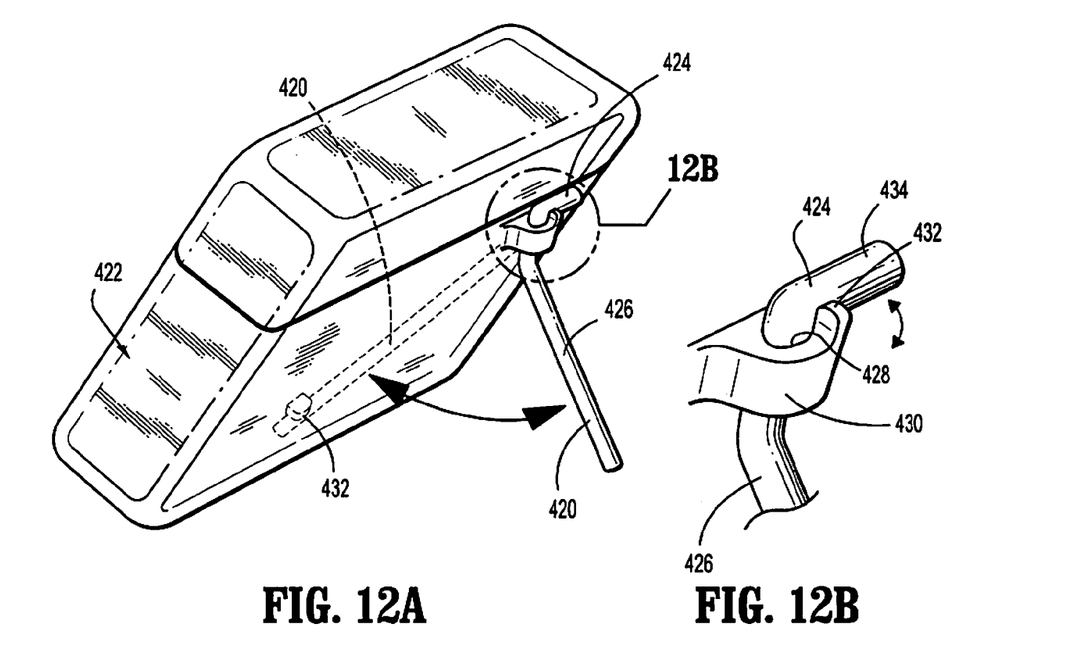
FIGS. 12A-12B are views of another alternate embodiment incorporating a rotatable leg member for supporting the subatmospheric pressure mechanism.

FIGS. 12A-12B illustrate another embodiment of elevation member. Elevation member 420 is in the form of a leg mounted for rotational movement relative to collection canister 422. Leg 420 defines an elongated element having a mounting segment 424 and a supporting segment 426 obliquely arranged relative to the mounting segment 424. Mounting segment 424 is accommodated within an aperture or opening 428 in collection canister 422 and may rotate within the opening 428 to selectively deploy leg 420. Opening 428 may be defined within a mounting extension 430 of collection canister 422.

Leg 420 is adapted to rotate between the first ambulatory position (shown in phantom) and the second supporting position depicted in FIG. 12A. In the first ambulatory position, leg 420 may be at least partially accommodated within locking recess 432 defined in the surface of collection canister 422. In one embodiment, the canister surfaces defining locking recess 432 engage leg 420 in a snap-fit relation therewith to releasably secure the leg 420 in the first ambulatory position. The snap-fit may provide a tactile and audible indication that the leg 420 is secured in the first ambulatory position. Mounting extension 430 of collection canister 422 defines a locking ledge 432 which engages offset segment 434 of mounting segment 424 of leg 420 when the leg 420 is in the second supporting position in, e.g., snap relation, to releasably secure the leg 420 in the second supporting position. This relationship also may provide a tactile and audible indication that the leg 420 is secured in the second supporting position.

Figure 13:
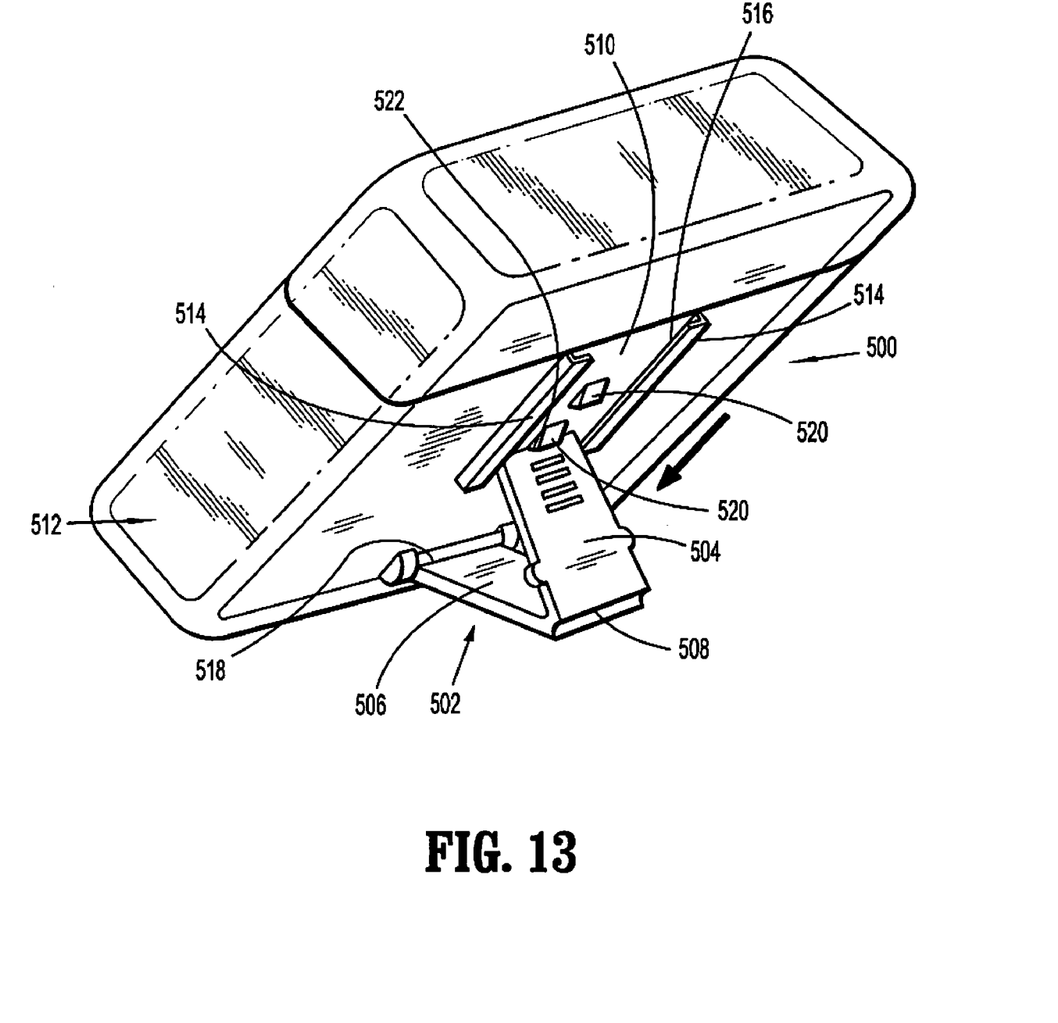
FIG. 13 is a perspective view of another embodiment of the subatmospheric pressure mechanism incorporating a hinged leg member.

FIG. 13 illustrates an alternate embodiment of subatmospheric pressure mechanism 500. In accordance with this embodiment, elevation member of the subatmospheric pressure mechanism includes hinge member 502. Hinge member 502 defines first and second hinge sections 504, 506 adapted to pivot relative to each other through a living hinge 508. In the alternative, a mechanical or pivot pin arrangement may couple first and second hinge sections 504, 506 for pivotal movement. First hinge section 504 is adapted to traverse a track 510 defined on the surface of collection canister 512 to move hinge member 502 between ambulatory and operative positions. Track 512 incorporates a pair of opposed rails 514 which receive a pair of opposed pins 516 depending from the sides of first hinge section 504. Pins 516 travel within rails 514 during movement of hinge member 502 between the ambulatory and operative positions. Second hinge section 506 is pivotally connected to the lower surface area of collection canister 512 through a mechanical or living hinge 518. As a further feature, collection canister 512 includes a plurality of spaced steps 520 on its surface to secure first hinge section 504 relative to collection canister 512 when deployed. The multiple number of steps 520 provides some flexibility to the subject to orient collection canister 512 at a desired orientation relative to the support surface. During deployment, first hinge section 504 and/or step 520 may deflect to permit passage of the upper edge 522 of the first hinge section 504 whereby upon clearing the step 520, the first hinge section 504 and/or step 520 returns to its initial condition. In this position, upper edge 522 of first hinge section 504 engages one of steps 520 in secured relation therewith.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A portable or semi-portable system for subatmospheric pressure therapy in connection with healing a surgical wound, which comprises:
   a wound dressing dimensioned for positioning relative to a wound bed of a subject;
   a subatmospheric pressure mechanism dimensioned to be carried or worn by the subject, the subatmospheric pressure mechanism including a housing, a vacuum source at least partially disposed within the housing and in fluid communication with the wound bed, a filter in fluid communication with the vacuum source, and a collection canister for collecting exudates from the wound bed removed under subatmospheric pressure, and
   an elevation member mounted with respect to the housing, the elevation member adapted to position the housing and the canister at a predetermined orientation when positioned relative to a support surface to minimize a potential of at least one of spillage of the exudates from the canister or clogging of the filter, the elevation member being a stand member positionable on the support surface and adapted for movement to vary a dimensioning of the stand member, the stand member defining a longitudinal axis extending along a length of the housing and including at least one support member rotatable about the longitudinal axis.

2. The system according to claim 1 wherein the stand member is dimensioned to define a cradle for at least partial reception of the housing or the canister.

3. The system according to claim 1 wherein the stand member includes at least two support members, the support members adapted for relative movement to provide enhanced supporting characteristics to the elevation member.

4. The system according to claim 3 wherein the support members are adapted for relative pivotal movement between an initial position and a pivoted position.

5. The system according to claim 4, further comprising a pivot element extending at least partially though the support members to provide relative pivotable movement between the support members.

6. The system according to claim 1, wherein the at least one support member is rotatable from a first position substantially aligned with the longitudinal axis and a second position transverse to the longitudinal axis.

7. The system according to claim 6, wherein the at least one support member is positionable in any position intermediate the first and second positions.

8. A system for subatmospheric pressure therapy in connection with healing a wound, which comprises:
   a wound dressing dimensioned for positioning relative to a wound bed of a subject;
   a subatmospheric pressure mechanism including a housing, a vacuum source at least partially disposed within the housing and in fluid communication with the wound bed, a filter in fluid communication with the vacuum source, and a collection canister; and
   an elevation member mountable to the housing, the elevation member adapted to position the housing and the canister at a predetermined orientation when positioned relative to a support surface, the elevation member being positionable on the support surface and defining a longitudinal axis extending along a length of the housing and including at least one support member rotatable about the longitudinal axis.

* * * * *